US010100636B2

(12) United States Patent
Pomerantz et al.

(10) Patent No.: US 10,100,636 B2
(45) Date of Patent: Oct. 16, 2018

(54) BITUMEN QUANTIFICATION USING VIBRATIONAL SPECTROSCOPY

(71) Applicant: Geoservices Equipements SAS, Roissy en France (FR)

(72) Inventors: Andrew Emil Pomerantz, Lexington, MA (US); Robert Leonard Kleinberg, Cambridge, MA (US); Ravinath Kausik Kadayam Viswanathan, Boston, MA (US); Paul Ryan Craddock, Scituate, MA (US)

(73) Assignee: GEOSERVICES EQUIPEMENTS, Roissy en France (FR)

( * ) Notice: Subject to any disclaimer, the term of this patent is extended or adjusted under 35 U.S.C. 154(b) by 289 days.

(21) Appl. No.: 14/898,514

(22) PCT Filed: Jun. 23, 2014

(86) PCT No.: PCT/US2014/043608
§ 371 (c)(1),
(2) Date: Dec. 15, 2015

(87) PCT Pub. No.: WO2014/209854
PCT Pub. Date: Dec. 31, 2014

(65) Prior Publication Data
US 2016/0138392 A1    May 19, 2016

Related U.S. Application Data

(60) Provisional application No. 61/839,277, filed on Jun. 25, 2013.

(51) Int. Cl.
*E21B 49/02*    (2006.01)
*E21B 49/00*    (2006.01)
(Continued)

(52) U.S. Cl.
CPC .............. *E21B 49/003* (2013.01); *E21B 7/00* (2013.01); *E21B 21/066* (2013.01); *E21B 25/00* (2013.01);
(Continued)

(58) Field of Classification Search
CPC ...... E21B 43/16; E21B 43/2401; E21B 43/38; E21B 49/00; E21B 49/02; E21B 21/066; E21B 43/241; E21B 49/005
See application file for complete search history.

(56) References Cited

U.S. PATENT DOCUMENTS 4,337,396 A    6/1982    Lauer et al.
4,433,239 A    2/1984    Thompson
(Continued)

OTHER PUBLICATIONS

International Search Report and Written Opinion issued in International App. No. PCT/US2014/043608 dated Oct. 24, 2014.
(Continued)

*Primary Examiner* — Zakiya W Bates
(74) *Attorney, Agent, or Firm* — Michael Dae

(57) ABSTRACT

Levels of kerogen and bitumen are computed in a sample of rock from DRIFTS measurements on the sample. The DRIFTS spectrum of a rock sample is measured, resulting in an estimate of bitumen and kerogen. Bitumen is then washed from the rock and DRIFTS is re-measured, resulting in an estimate of kerogen. Bitumen quantity is calculated by subtracting the washed sampled results from first DRIFTS measurements.

20 Claims, 2 Drawing Sheets

(51) Int. Cl.
*E21B 21/06* (2006.01)
*G01N 21/3563* (2014.01)
*G01N 21/47* (2006.01)
*G01N 21/552* (2014.01)
*G01N 21/65* (2006.01)
*E21B 7/00* (2006.01)
*E21B 25/00* (2006.01)
*G01N 33/28* (2006.01)
*G01N 21/35* (2014.01)

(52) U.S. Cl.
CPC ..... *G01N 21/3563* (2013.01); *G01N 21/4738* (2013.01); *G01N 21/552* (2013.01); *G01N 21/65* (2013.01); *G01N 33/2823* (2013.01); *G01N 2021/3595* (2013.01); *G01N 2021/4769* (2013.01)

(56) References Cited

U.S. PATENT DOCUMENTS

| | | |
|---|---|---|
| 8,967,249 B2 | 3/2015 | Akkurt et al. |
| 2010/0089132 A1 | 4/2010 | Larter et al. |
| 2012/0192639 A1 | 8/2012 | Valenza, II et al. |
| 2013/0046469 A1 | 2/2013 | Herron et al. |
| 2013/0112406 A1 | 5/2013 | Zuo et al. |
| 2013/0269933 A1 | 10/2013 | Pomerantz et al. |
| 2013/0273661 A1 | 10/2013 | Pomerantz |
| 2015/0022202 A1* | 1/2015 | Song .................. G01V 3/14 324/307 |

OTHER PUBLICATIONS

Jarvie, D. M., 2012, Shale resource systems for oil and gas: Part 2—Shale-oil resource systems, in J. A. Breyer, ed., Shale reservoirs—Giant resources for the 21st century: AAPG Memoir 97, p. 89-119.

International Preliminary report on patentability issued in the related PCT application PCT/US2014/043608, dated Dec. 29, 2015 (11 pages).

The extended search report issued in the related EP Application 14818266.0, dated Apr. 18, 2017 (6 pages).

H.H. Ganz et al., "IR Classification of Kerogen type, thermal maturation, hydrocarbon potential and lithological charateristics", Journal of Southeast Asian Earth Sciences, vol. 5, No. 1-4, 1991, pp. 19-28.

* cited by examiner

BITUMEN QUANTIFICATION USING VIBRATIONAL SPECTROSCOPY

CROSS-REFERENCE TO RELATED APPLICATIONS

This patent application claims the benefit of: U.S. Prov. Ser. No. 61/839,277, filed 25 Jun. 2013, which is incorporated by reference herein.

FIELD

The subject disclosure generally relates to methods and systems for evaluating the producibility of formations. More particularly, the subject disclosure relates to analyzing earth samples using vibrational spectroscopy to quantifying amounts of kerogen and/or bitumen contained therein.

BACKGROUND

In the maturation of a tight oil reservoir, the conversion of kerogen to oil and gas typically involves the formation of a heavy, immobile intermediate referred to as bitumen. Bitumen is typically present at varying levels as a component in tight oil reservoirs. Residual bitumen can clog pores in the rock and especially pores hosted in the kerogen. As a result, the quantity of bitumen in a reservoir rock can have a dramatic effect on the permeability and, therefore, on overall reservoir quality.

Known methods for quantifying bitumen levels in rocks samples exist, such as Soxhlet extraction. However, such conventional techniques are relatively time consuming.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method quantifying amounts of bitumen in an earth sample is described. The method includes: analyzing the earth sample using vibrational spectroscopy to generate data indicating a combined quantity of kerogen and bitumen in the earth sample; washing the earth sample, e.g. using at least an organic solvent, thereby removing bitumen from the earth sample; analyzing the washed earth sample using vibrational spectroscopy to generate data indicating a quantity of kerogen in the washed earth sample; and determining a quantity of bitumen in the earth sample by subtracting analysis results of washed earth sample from results of the earth sample. According to some embodiments, the vibrational spectroscopy is diffuse reflectance infrared Fourier transform spectroscopy (DRIFTS). According to other embodiments, other types of vibrational spectroscopy are used such as Raman spectroscopy, transmission Fourier transform infrared spectroscopy (FTIR), or attenuated total reflection (ATR).

According to some embodiments, the earth sample is obtained from drilling cuttings such as from a drilling operation using water-based drilling mud. The drilling operation can be altered based on the determined quantity of bitumen. According to some embodiments, the earth sample is obtained from a core sample or an outcropping. According to some embodiments, the earth sample is from a tight oil reservoir. According to some embodiments, the organic solvent includes pentane, hexane, heptane, acetone, toluene, benzene, xylene, chloroform, dichloromethane, and/or a combination thereof.

According to some embodiments, a system is described for quantifying amounts of bitumen in an earth sample. The system includes an earth sample washing system configured to remove bitumen from an earth sample thereby generating a washed earth sample; a vibrational spectroscopy system configured to analyze the earth sample and generate therefrom data indicating combined kerogen and bitumen in the unwashed earth sample; and to analyze an earth sample having bitumen washed therefrom by the washing system and generate data indicating kerogen in the washed earth sample. The system also includes a processing system configured to determine a quantity of bitumen by combining the data indicating the combined kerogen and bitumen in the earth sample with the data indicating the kerogen in the washed earth sample.

As used herein, the term "bitumen" refers to naturally occurring organic matter in a sedimentary rock that is soluble in organic solvents. Bitumen, as used herein, is immobile within the source rock, being typically solid or nearly so.

As used herein, the term "kerogen" refers to a naturally occurring, solid, insoluble organic matter in a sedimentary rock.

As used herein, the term "vibrational spectroscopy" refers to both Raman spectroscopy and infrared spectroscopy techniques, and includes, but is not limited to, Raman spectroscopy (both scattering and transmission), as well as infrared spectroscopy such as Diffuse Reflectance Infrared Fourier Transform Spectroscopy (DRIFTS), transmission Fourier transform infrared spectroscopy (FTIR), and Attenuated total reflectance (ATR).

Further features and advantages of the subject disclosure will become more readily apparent from the following detailed description, when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

Figure 1:
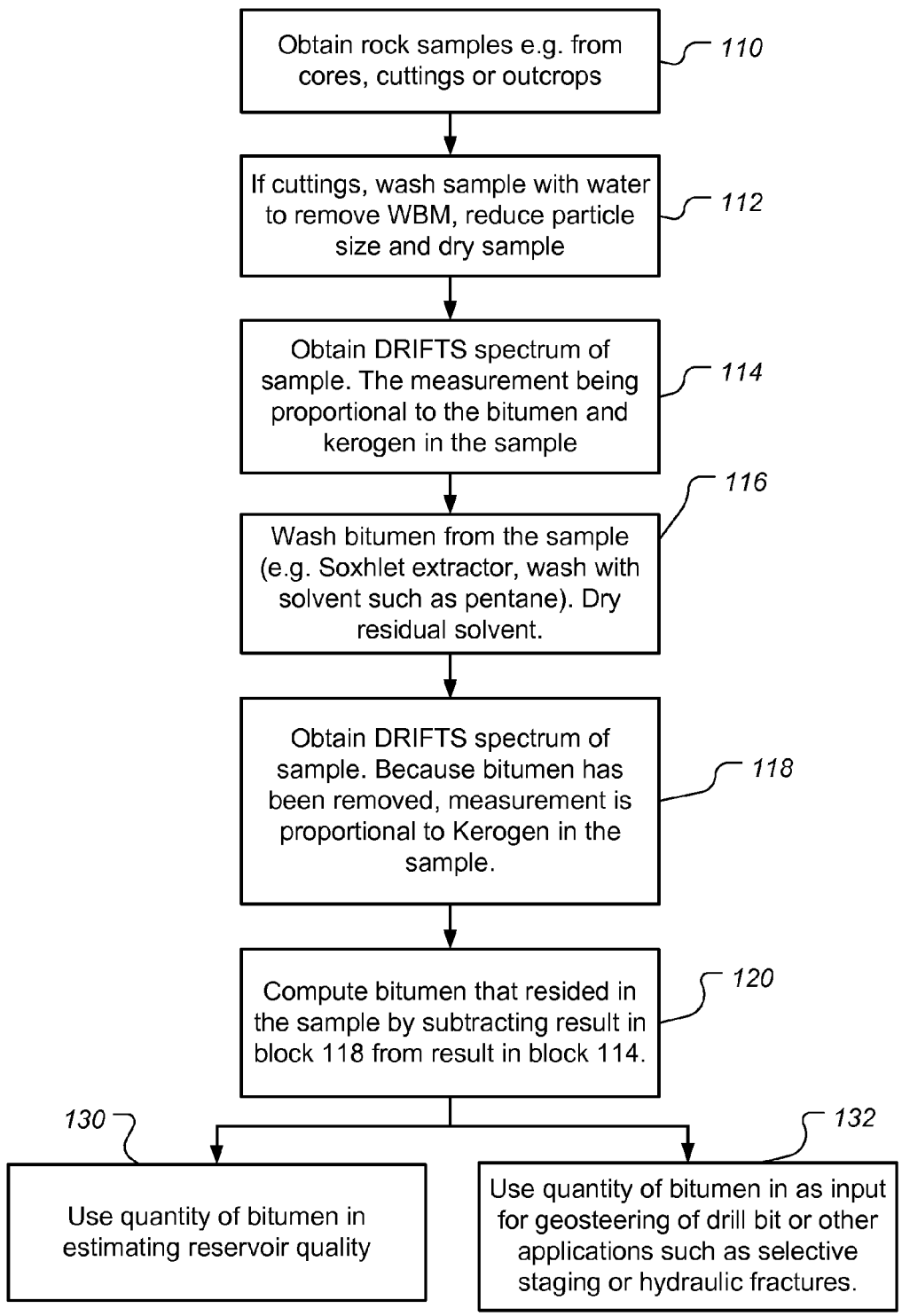
FIG. 1 is a flow chart illustrating some aspects of quantifying bitumen using vibrational spectroscopy, according to some embodiments.

The particulars shown herein are by way of example and for purposes of illustrative discussion of the embodiments of the subject disclosure only, and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, and the description taken with the drawings making apparent to those skilled in the art how the several forms of the subject disclosure may be embodied in practice.

Furthermore, like reference numbers and designations in the various drawings indicate like elements.

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming, but would nevertheless be a routine undertaking for those of ordinary skill in the art having the benefit of this disclosure. In addition, the composition used/disclosed herein can also comprise some components other than those cited. In the summary of the invention and this detailed description, each numerical value should be read once as modified by the term "about" (unless already expressly so modified), and then read again as not so modified, unless otherwise indicated in context. Also, in the summary of the invention and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

Tight oil (also referred to as shale oil or light tight oil, abbreviated LTO) is a petroleum play that consists of light crude oil contained in petroleum-bearing formations of low permeability, often shale or tight sandstone. In many tight oil plays, transport of mobile hydrocarbon goes through inorganic-hosted as well as organic-hosted pores. In these systems, bitumen can clog these pores thereby rendering a portion of the oil non-producible. The producibility of these formations is therefore related to the abundance of bitumen in the rock. According to some embodiments, techniques are disclosed for measuring the quantities of kerogen and bitumen using diffuse reflectance infrared Fourier transform spectroscopy (DRIFTS). In a non-limiting example, the rock sample may derive from cores, cuttings, and/or outcrops. The DRIFTS measurements may be performed at the wellsite or in a laboratory. In the case of drilling cuttings used for DRIFTS measurement, the wells should be drilled with a water-based-mud (WBM) rather than an oil-based-mud (OBM).

According to some embodiments, levels of kerogen and bitumen are computed in a sample of rock from DRIFTS measurements on the sample. According to some embodiments, the described method comprises measuring the DRIFTS spectrum of an entire rock, resulting in an estimate of bitumen and kerogen. Bitumen is then washed from the rock and DRIFTS is re-measured, resulting in an estimate of kerogen.

FIG. 1 is a flow chart illustrating some aspects of quantifying bitumen using vibrational spectroscopy, according to some embodiments. In block 110, a sample of rock is collected. In non-limiting examples, this sample of rock may be cores, cuttings, or from an outcrop. The location including the depth of where the sample originated is noted. The sample should not have been exposed to hydrocarbons that include oil-based muds (OBM).

In block 112, if the sample comes from drilling cuttings, the sample is washed with water to remove water-based mud additives. The sample is crushed and dried. In block 114, the organic content of the sample is measured. According to some embodiments, DRIFTS measurement is used to measure the organic content of the sample. The DRIFTS measurement is proportional to the bitumen and kerogen in the sample.

In block 116, the bitumen is washed from the sample. This may include washing the sample in a Soxhlet extractor. According to some embodiments, a quicker process is used in which the samples is crushed and washed over a sieve or vacuum filter using a solvent such as pentane. Note that the kerogen is not washed from the sample since it is insoluble in organic solvents. For further details of such washing processes, see e.g. co-pending U.S. Patent Application Publ. No. 2013-0269933, which is incorporated herein by reference. Residual solvent is then dried from the sample using, for example, evaporation.

In block 118, the organic content of the sample is measured using, for example, DRIFTS. As the bitumen has been removed, this measurement is proportional to the kerogen. According to some embodiments, another form of vibrational spectroscopy measurement is used in blocks 114 and 118 instead of DRIFTS. For example, according to some embodiments infrared spectroscopy such as Raman spectroscopy, transmission Fourier transform infrared spectroscopy (FTIR), or Attenuated total reflection (ATR) is used in blocks 114 and 118.

In block 120, the bitumen content of the sample is computed by subtracting the results in block 118 (kerogen only) from block 114 (kerogen and bitumen).

According to some embodiments, the calculated bitumen amount is used to identify productive zones in a tight oil play, for geosteering or selective staging of hydraulic fractures (block 132). According to some other embodiments, the calculated bitumen amount is used to estimate reservoir quality and/or for other formation evaluation purposes.

Figure 2:
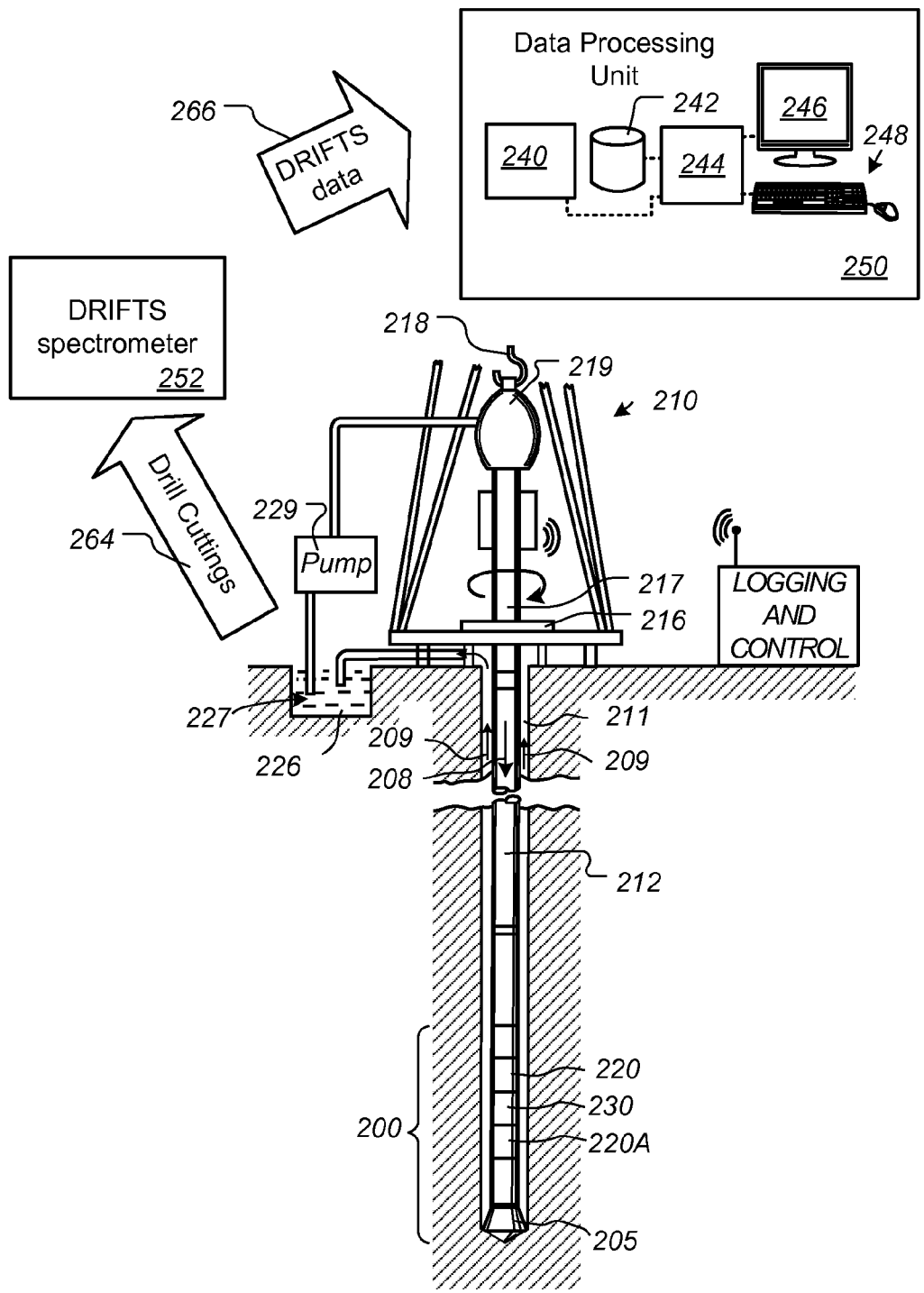
FIG. 2 is a diagram illustrating a wellsite system in which bitumen can be determined from DRIFTS analysis of drill cuttings while drilling, according to some embodiments.

FIG. 2 is a diagram illustrating a wellsite system in which bitumen can be determined from DRIFTS analysis of drill cuttings while drilling, according to some embodiments. The wellsite can be onshore or offshore. In this exemplary system, a borehole 211 is formed in subsurface formations by rotary drilling in a manner that is well known. Embodiments of the invention can also use directional drilling, as will be described hereinafter.

A drill string 212 is suspended within the borehole 211 and has a bottom hole assembly 200 that includes a drill bit 205 at its lower end. The surface system includes platform and derrick assembly 210 positioned over the borehole 211, the assembly 210 including a rotary table 216, kelly 217, hook 218 and rotary swivel 219. The drill string 212 is rotated by the rotary table 216, energized by means not shown, which engages the kelly 217 at the upper end of the drill string. The drill string 212 is suspended from a hook 218, attached to a traveling block (also not shown), through the kelly 217 and a rotary swivel 219, which permits rotation of the drill string relative to the hook. As is well known, a top drive system could alternatively be used.

In the example of this embodiment, the surface system further includes drilling fluid or mud 226, stored in a pit 227 formed at the well site. A pump 229 delivers the drilling fluid 226 to the interior of the drill string 212 via a port in the swivel 219, causing the drilling fluid to flow downwardly through the drill string 212, as indicated by the directional arrow 208. The drilling fluid exits the drill string 212 via ports in the drill bit 205, and then circulates upwardly through the annulus region between the outside of the drill string and the wall of the borehole, as indicated by the directional arrows 209. In this well-known manner, the drilling fluid lubricates the drill bit 205 and carries formation cuttings up to the surface as it is returned to the pit 227 for recirculation.

The bottom hole assembly 200 of the illustrated embodiment contains a logging-while-drilling (LWD) module 220, a measuring-while-drilling (MWD) module 230, a rotosteerable system and motor, and drill bit 205.

The LWD module 220 is housed in a special type of drill collar, as is known in the art, and can contain one or a plurality of known types of logging tools. It will also be understood that more than one LWD and/or MWD module can be employed, e.g. as represented at 220A. (References throughout, to a module at the position of 220, can alternatively mean a module at the position of 220A as well.) The LWD module includes capabilities for measuring, processing, and storing information, as well as for communicating with the surface equipment. In the present embodiment, the LWD module includes a resistivity measuring device as well as a number of other devices, such as a neutron-density measuring device.

The MWD module 230 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

According to some embodiments, drill cuttings 264 are taken from the drilling mud, cleaned and analyzed using DRIFTS spectrometer 252 (such as shown in blocks 110, 112, 114, 116 and 118 of FIG. 1). The data 266 from the DRIFTS spectrometer 252 is processed by a processing unit 250. Unit 250 can be located in a logging truck or at some other location at the wellsite. According to some embodiments, data processing unit 250 is located at one or more locations remote from the wellsite. The processing unit 250 preferably includes one or more central processing units 244, storage system 242, communications and input/output modules 240, a user display 246 and a user input system 248. According to some embodiments, computations and analysis as shown in FIG. 1 are carried out while drilling in unit 250. According to some embodiments, the computer programs and hardware shown unit 250 may be distributed across devices including, but not limited to, tooling which is inserted into the borehole and equipment which is located at the surface, whether onsite or elsewhere.

According to some embodiments bitumen and kerogen data determined by the DRIFTS spectrometer 252 and data processing unit 250 are used to alter the drilling operation. For example, as shown in block 132 of FIG. 1, the bitumen data can be used as an input for geosteering, for example using a roto-steerable system and motor in bottom hole assembly 200.

For further detail regarding implementation of diffuse reflectance infrared Fourier transform spectroscopy (DRIFTS), according to some embodiments, please refer to (1) co-owned United States Patent Publ. No.: 2013/0273661 entitled "Method and apparatus for simultaneous estimation of quantitative mineralogy, kerogen content and maturity in gas shale and oil-bearing shale", filed Apr. 13, 2012; and (2) United States Patent Publication No.: 2013/0046469, entitled "Diffuse reflectance infrared Fourier transform spectroscopy for characterization of earth materials" filed Aug. 10, 2012, both of which incorporated by reference herein in their entirety.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method quantifying amounts of bitumen in an earth sample comprising:
    analyzing the earth sample using vibrational spectroscopy to generate a first set of data indicating a combined quantity of kerogen and bitumen in the earth sample;
    washing the earth sample, thereby removing bitumen from the earth sample, after analyzing the earth sample using vibrational spectroscopy, thereby generating a washed earth sample;
    analyzing the washed earth sample using vibrational spectroscopy to generate a second set of data indicating a quantity of kerogen in the washed earth sample; and
    determining a quantity of bitumen in the earth sample by combining the first set of data indicating the combined quantity of kerogen and bitumen in the earth sample with the second set of data indicating the quantity of kerogen in the washed earth sample.

2. A method according to claim 1 wherein said washing the earth sample uses at least an organic solvent.

3. A method according to claim 2 wherein said organic solvent includes one or more components selected from a group consisting of: pentane, hexane, heptane, acetone, toluene, benzene, xylene, chloroform, and dichloromethane.

4. A method according to claim 1 wherein the vibrational spectroscopy is diffuse reflectance infrared Fourier transform spectroscopy (DRIFTS).

5. A method according to claim 1 wherein the vibrational spectroscopy is of a type selected from a group consisting of: Raman spectroscopy, transmission Fourier transform infrared spectroscopy (FTIR), and Attenuated total reflection (ATR).

6. A method according to claim 1 wherein the earth sample is obtained from drilling cuttings.

7. A method according to claim 6 wherein the drilling cuttings are generated from a drilling operation at a wellsite using water-based drilling mud, and wherein the method is carried out at said wellsite during said drilling operation.

8. A method according to claim 7 further comprising altering said drilling operation based at least in part on said determined quantity of bitumen.

9. A method according to claim 7 further comprising pre-washing the earth sample prior to said analyzing the earth sample to generate the first set of data indicating a combined quantity of kerogen and bitumen, wherein said pre-washing comprises washing with water to remove said water-based drilling mud.

10. A method according to claim 7 wherein said method is carried out in a location remote from said wellsite.

11. A method according to claim 1 wherein the earth sample is obtained from a core sample or an outcropping.

12. A method according to claim 1 wherein said earth sample is from a tight oil reservoir.

13. A method according to claim 1 further comprising estimating a reservoir quality value based at least in part on the determined quantity of bitumen.

14. A system for quantifying amounts of bitumen in an earth sample, comprising:
 an earth sample washing system configured to remove bitumen from an earth sample after the earth sample is analyzed by a vibrational spectroscopy system, thereby generating a washed earth sample;
 the vibrational spectroscopy system configured to analyze the earth sample and generate therefrom a first set of data indicating combined kerogen and bitumen in the earth sample, and to analyze the washed earth sample having bitumen washed therefrom by the washing system and generate therefrom a second set of data indicating kerogen in the washed earth sample; and
 a processing system configured to determine a quantity of bitumen by combining the first set of data indicating the combined kerogen and bitumen in the earth sample with the second set of data indicating the kerogen in the washed earth sample.

15. A system according to claim 14 wherein said washing system includes the use of at least an organic solvent.

16. A system according to claim 15 wherein said organic solvent includes one or more components selected from a group consisting of: pentane, hexane, heptane, acetone, toluene, benzene, xylene, chloroform, and dichloromethane.

17. A system according to claim 14 wherein the vibrational spectroscopy is diffuse reflectance infrared Fourier transform spectroscopy (DRIFTS).

18. A system according to claim 14 wherein said system is configured for deployment at a wellsite and said earth sample is gathered from drill cuttings.

19. A system according to claim 18 further comprising a drilling control system configured to alter a drilling operation based at least in part on said determined quantity of bitumen.

20. A system according to claim 14 wherein the vibrational spectroscopy is of a type selected from a group consisting of: Raman spectroscopy, transmission Fourier transform infrared spectroscopy (FTIR), and Attenuated total reflection (ATR).

\* \* \* \* \*